United States Patent [19]

Fenoglio et al.

[11] Patent Number: 5,080,815

[45] Date of Patent: Jan. 14, 1992

[54] METHOD FOR PREPARING ENGINE SEAL COMPATIBLE DISPERSANT FOR LUBRICATING OILS COMPRISING REACTING HYDROCARBYL SUBSTITUTED DICARBOXYLIC COMPOUND WITH AMINOGUANIRISE OR BASIC SALT THEREOF

[75] Inventors: David J. Fenoglio, Wheaton; Paula R. Vettel, Downers Grove; David W. Eggerding, Naperville, all of Ill.

[73] Assignee: Amoco Corporation, Chicago, Ill.

[21] Appl. No.: 292,414

[22] Filed: Dec. 30, 1988

Related U.S. Application Data

[63] Continuation-in-part of Ser. No. 103,169, Sep. 30, 1987, Pat. No. 4,908,145.

[51] Int. Cl.$^5$ .................. C10M 133/44; C10M 105/70
[52] U.S. Cl. ............................. 252/51.5 A; 252/351; 252/357; 548/262.2; 548/262.4; 548/262.8
[58] Field of Search ................. 252/51.5 A, 351, 356, 252/357

[56] References Cited

U.S. PATENT DOCUMENTS

| | | | |
|---|---|---|---|
| 3,272,746 | 9/1966 | Le Suer | 252/51.5 A |
| 3,341,542 | 9/1967 | Le Suer | 252/51.5 A |
| 4,491,527 | 1/1985 | Lange | 252/51.5 A |
| 4,908,145 | 3/1990 | Fenoglio | 252/51.5 A |

FOREIGN PATENT DOCUMENTS 0998869 6/1965 United Kingdom .

Primary Examiner—Prince Willis, Jr.
Assistant Examiner—Ellen McAvoy
Attorney, Agent, or Firm—Matthew R. Hooper; William H. Magidson; Ralph C. Medhurst

[57] ABSTRACT

A dispersant composition having improved compatibility with fluorohydrocarbon-containing elastomeric engine seals, said dispersant composition comprising the reaction product obtained by reacting a $C_{30}$–$C_{250}$ hydrocarbyl-substituted succinic anhydride with aminoguanidine, or a basic salt thereof, at a reaction temperature of from about 155° C. to about 200° C.

26 Claims, No Drawings

METHOD FOR PREPARING ENGINE SEAL COMPATIBLE DISPERSANT FOR LUBRICATING OILS COMPRISING REACTING HYDROCARBYL SUBSTITUTED DICARBOXYLIC COMPOUND WITH AMINOGUANIRISE OR BASIC SALT THEREOF

This application is a continuation-in-part of Ser. No. 103,169 filed Sept. 30, 1987, now U.S. Pat. No. 4,908,145.

BACKGROUND OF THE INVENTION

1. Field of the Invention

The present invention relates generally to nitrogen-containing dispersants for lubricating oils obtained by reacting a long chain hydrocarbyl-substituted succinic acid or anhydride with an amine, and lubricating oils incorporating such dispersants. More particularly, the invention is directed to a lubricating oil dispersant having markedly improved compatibility toward fluorohydrocarbon elastomer engine seals, a method for making the dispersant, and lubricating compositions (including additive concentrates) incorporating the dispersant. The dispersant composition of the present invention comprises the reaction product obtained by reacting a long chain hydrocarbyl-substituted succinic acid or anhydride with aminoguanidine or basic salt thereof in a ratio of about 1.4 to about 2.2 moles of aminoguanidine, or basic salt thereof, per equivalent of hydrocarbyl succinic acid or anhydride, at a temperature of from about 155° C. to about 200° C. In its several related embodiments the present invention is further directed to a combination of the above dispersant and a polymeric dispersant-VI improver and/or an alkaline earth phenate detergent.

2. Description of the Prior Art

The presence of water and precursors of sludge in lubricating oils constitutes a very serious problem that is associated with crankcase lubricating oils. There occurs in the lubricating oil various foreign particles, such as dirt, soot, and products of decomposition that result from the breakdown of the lubricating oil. The combination of water and such foreign particles results in the deposition of sludge which has a deleterious effect upon the efficient operation of the engine containing the lubricating oil. In order to prevent the deposition of the sludge, various detergents and dispersants are added to the lubricating oil composition.

While the nitrogen dispersants have been used to prevent sludge, varnish and lacquer deposits in lube oils intended for passenger car engines, it is well known that the alkaline earth metal phenate detergents perform a similar function in diesel engines. High levels of nitrogen dispersant and phenate detergent are now required if a lubricant formulation is to pass the latest passenger car test specifications (SG) as well as the latest diesel engine test specifications (CD or CE). Unfortunately, it is frequently necessary for such formulations to also pass engine tests measuring the compatibility of the lubricant with elastomeric engine seals.

Flexible engine seals are used in assembling internal combustion engines to prevent leakage of lubricants at those points where moving parts, such as crankshafts, extend outside the engine block. Because leakage of the lubricant from the internal combustion crankcase is very undesirable, an important consideration when selecting a dispersant for use in the lubricating oil composition is its compatibility with fluorohydrocarbon crankshaft seals. These seals very often comprise fluorohydrocarbon elastomers which are attacked by the dispersant.

When conventional nitrogen dispersants are present in lubricating compositions at passing SG levels, many such compositions will fail the elastomer seal tests. When phenates, especially calcium phenates, are added to the oil along wit the conventional nitrogen dispersants, elastomer compatibility is worse. The problem of seal compatibility is also worsened if, in addition to the nitrogen dispersant, a nitrogen-containing polymeric dispersant-VI improver is present in the lubricant composition. The nitrogen in dispersant-VI improvers, while particularly effective at controlling engine deposits, is generally quite harmful to elastomer engine seals.

Given the problems outlined above, there is needed a dispersant which is sufficiently passive toward fluorohydrocarbon seals that lubricant formulations containing high levels of the dispersant, to meet SG specifications, can also pass engine seal compatibility tests, especially when the lubricant formulations must also comprise high levels of phenate detergent necessary to meet CD or CE diesel engine specifications, or when the formulations include a nitrogen-containing dispersant-VI improver.

In U.S. Pat. No. 4,379,064, Cengel, et al. discloses the passivation of polyamine dispersants to fluorohydrocarbon engine seal compositions that are employed in internal combustion engines by the mild oxidation of such polyamine dispersants.

In U.S. Pat. Nos. 3,272,746 and 3,341,542, Le Suer, et al. disclose lubricating oil compositions containing acylated nitrogen compounds prepared, for example, by reacting a substituted succinic acid or derivative thereof with a nitrogen-containing compound, such as ammonia, aliphatic amines, aromatic amines, heterocyclic amines, or carboxylic amines. The resulting detergent composition comprises an oil-soluble, acylated nitrogen composition characterized by the presence within its structure of (a) a substantially hydrocarbon-substituted polar group selected from the class consisting of acyl, acylimidoyl, and acyloxy radicals wherein the substantially hydrocarbon substituent contains at least about 50 aliphatic carbon atoms and (b) a nitrogen-containing group characterized by a nitrogen atom attached directly to said relatively polar group. Example 38 of these patents teaches reaction of polyisobutene-substituted succinic anhydride and aminoguanidine bicarbonate at a temperature in the range of 130° C. (266° F.) to 165° C. (329° F.). The resulting product is taught for use as a lubricating oil additive and is said to be an effective dispersant. These patents teach that the mixture of acid-producing compound and the nitrogen-containing reactant is usually heated at a temperature above 80° C. (176° F.), preferably within the range of about 100° C. (212° F.) to about 250° C. (482° F.). The patents disclosed aminoguanidines and other guanidines among a host of possible sources of nitrogen-containing compounds. For example, guanidine, 1,3-diphenylguanidine, and 1,2,3-tributylguanidine are disclosed. These patents, however, do not teach or suggest that the resulting dispersants can comprise triazoles, much less specific temperatures one must employ to obtain a dispersant which is predominantly triazole. There is also no teaching or suggestion in these patents as to the relative compatibility toward engine seals of the many different reaction products disclosed. Thus, apart from the fact that the teachings of the '746 and '542 patents are too broad to anticipate or render obvious the present invention, the patents are not even directed to the problem addressed by the present invention, namely, how to formulate a nitrogen-containing dispersant that provides excellent dispersancy and detergency but is also mild toward engine seals of the fluorohydrocarbon type.

In U.S. Pat. No. 4,491,527, Lange, et al. disclosed ester-heterocycle compositions useful as "lead paint" inhibitors and lubricants, e.g., compositions comprising a major proportion of a pentaerythritol ester of an alkenyl succinic acid in which the alkenyl group contains at least about 30 carbon atoms and a minor proportion of a heterocyclic condensation product of said alkenyl succinic acid derived from a 5-membered ring heterocycle containing at least 2 ring hetero atoms separated by a single carbon atom, at least one of said hetero atoms being nitrogen. The heterocyclic condensation product is characterized by the presence of at least one heterocyclic moiety including a 5- or 6-membered ring which contains at least 2 ring hetero atoms, separated by a single carbon atom. Such ring hetero atoms may be oxygen, sulfur, and nitrogen, with at least one thereof being nitrogen. Most often, the heterocyclic moiety contains a maximum of three hetero atoms and a 5-membered ring, preferably, a triazole or thiadiazole ring, and, most desirably, a 1,2,4,-triazole ring. This patent teaches that aminoguanidine and salts of aminoguanidine, such as aminoguanidine bicarbonate, are examples of acyclic heterocycle precursors which may be reacted with the proper acid or acid derivative group. Like the patents discussed above, Lange '527 is not at all concerned with the problem of seal degradation caused by nitrogen-containing dispersants. Lange '527 does not disclose or suggest the invention presently described.

An object of the present invention is to provide a lubricating oil dispersant composition, as well as an additive concentrate or lubricant composition incorporating such dispersant, in which the nitrogen-containing moieties of the dispersant compound are compatible with fluorohydrocarbon-containing elastomeric engine seals. Other objects will be apparent to those skilled in the art.

SUMMARY OF THE INVENTION

The present invention is directed to a dispersant composition having improved compatibility toward fluorohydrocarbon-containing elastomeric engine seals, said dispersant composition comprising the reaction product obtained by reacting a hydrocarbyl substituted dicarboxylic compound selected from the group consisting of hydrocarbyl substituted dicarboxylic acids, hydrocarbyl substituted dicarboxylic acid anhydrides, and mixtures thereof, said hydrocarbyl substituent being about $C_{30}-C_{250}$, with aminoguanidine or a basic salt thereof, at a reaction temperature of from about 155° C. to about 200° C. and in a ratio of about 1.4 to about 2.2 moles of aminoguanidine or basic salt thereof per equivalent of hydrocarbyl substituted dicarboxylic compound.

The invention is further directed to a composition suitable as a dispersing agent for lubricating oils, wherein the composition comprises a mixture of dispersant compounds having nitrogen-containing groups, said mixture comprising (a) at least one dispersant compound which is incompatible with fluorohydrocarbon-containing engine seals or which elicits poor or marginal compatibility with such seals; and (b) a dispersant compound obtained by reacting a hydrocarbyl substituted dicarboxylic compound selected from the group consisting of hydrocarbyl substituted dicarboxylic acids, hydrocarbyl substituted dicarboxylic acid anhydrides, and mixtures thereof. said hydrocarbyl substituent being about $C_{30}-C_{250}$, with aminoguanidine or a basic salt thereof, at a reaction temperature of from about 155° C. to about 200° C. and in a ratio of about 1.4 to about 2.2 moles of aminoguanidine or basic salt thereof per equivalent of hydrocarbyl substituted dicarboxylic compound, wherein the relative amounts of (a) and (b) in the mixture are such that the composition is compatible with fluorohydrocarbon elastomer engine seals.

In a related aspect, the present invention is directed to lubricating compositions containing a major amount of oil of lubricating viscosity and a minor effective dispersant amount of the dispersant compositions summarized above.

The present invention is further directed to concentrates for formulating lubricating compositions comprising from about 20 to about 90% by weight of a normally liquid, substantially inert organic solvent/diluent and from about 10% to about 80% of the dispersant composition(s) summarized above.

The present invention is also directed to lubricating compositions which combine the dispersant summarized above with a neutral or overbased phenate detergent, and/or with a dispersant-VI improver.

A principal advantage in the present invention is the compatibility of the described dispersant toward fluorohydrocarbon-containing elastomeric engine seals. Recently, the need for seal compatible dispersants has become great in formulating lubricants required to pass the latest engine test specifications, i.e. the SG/CD and SG/CE specifications. Such lubricants must contain higher levels of dispersant and detergent. Among the most effective dispersants are the nitrogen-containing compounds. Preferred detergents are the phenates. However, as pointed out above, these compounds are very aggressive toward fluorohydrocarbon engine seals. The present invention permits the use of higher amounts of the dispersant and detergent additive to meet recent requirements without the associated problem of engine seal degradation. Even the most severe elastomer tests such as the Volkswagen Viton ® test can be passed using an "SG" formulation prepared with a dispersant of the present invention.

The improved seal compatibility of the dispersant facilitates the use of increased levels of dispersant/VI improvers which have nitrogen groups that are harmful toward engine seals.

DETAILED DESCRIPTION

Briefly, the present invention is based on the discovery of a new nitrogen-containing dispersant that offers excellent dispersancy plus compatibility with fluorohydrocarbon elastomeric engine seals. The dispersant is the reaction product of a long chain hydrocarbyl-substituted dicarboxylic compound, preferably a polyalkenyl succinic anhydride such as polybutenyl succinic anhydride, and a basic aminoguanidine salt, preferably the bicarbonate, where the reaction is conducted at from about 155° C. to about 200° C. and preferably about 170° C. to 190° C., and at a ratio of aminoguanidine salt to succinic anhydride compound of from about 1.4 to about 2.2 moles per equivalent of anhydride, and preferably about 1.7 to 2.0 moles of aminoguanidine bicarbonate per equivalent of succinic anhydride. Present analysis indicates that the product comprises at least about 50 wt.% of the hydrocarbyl-substituted bis-3-amino-1,2,4-triazole having the structure below and tautomeric forms thereof:

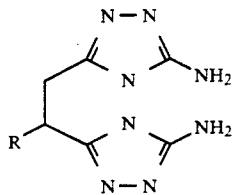

The phenate detergents contemplated for use in the present invention include any of the well-known neutral or overbased sulfurized phenates prepared by reacting an alkyl-substituted phenol, a sulfurizing agent, and a calcium or magnesium compound. The phenate can be carbonate overbased to contain an excess amount of metal in the form of carbonates or hydroxides, relative to the amount of neutral phenate. The preparation and use of such phenates are well known to those skilled in the art.

The dispersant-VI improvers contemplated for use in combination with the triazole dispersant of the present invention can comprise any of the well-known functionalized polymers that impart dispersancy to and improve the viscosity characteristics of a lubricating oil. As is well known to those skilled in the art, the polymeric backbone of the dispersant-VI improver can be prepared by polymerizing monomers such as ethylene, propylene, isobutylene, styrene, butadiene, alkyl acrylates and methacrylates, norbutadiene, isoprene, maleates, maleic anhydride, maleimides, carbon monoxide, vinyl-substituted amines and alcohols, etc. The molecular weight of the products is at least 5000, and is preferably at least 10,000. The polymers may contain oxygen functionality from shearing in air or oxygen or reaction with oxidizing agents. To provide dispersancy, the polymers contain amine, amide or alcohol groups in the monomers, or may be reacted with amines, amides or alcohols.

A lubricating oil composition in accordance with the present invention comprises a major amount of oil of lubricating viscosity and a minor effective dispersant amount of the seal compatible dispersant of the invention. A minor effective dispersant amount is from about 0.01 to about 10 and preferably from about 2 to about 8 wt. % of the finished oil. It should be pointed out that these dispersant amounts assume the dispersant composition will be about 35 to about 60% "active," meaning that the dispersant composition consists of about 35 to about 60 wt. % of the actual dispersant compound, the remainder being substantially inert organic diluent carrier fluid, such as neutral process oil, in which the dispersant is dissolved. In addition to neutral process oil, unreacted polybutene present in polybutenyl succinic anhydride is also intended to be encompassed by the term "substantially inert diluent." The inert diluent can be present during the preparation of the dispersant but can also be added to the dispersant, following preparation, to achieve a desired physical property such as viscosity.

Another lubricating composition of the present invention comprises the seal-compatible dispersant described herein combined with an alkaline earth metal phenate detergent. The phenate detergent can be present in an amount of from about 0.2 to 27% by weight of the composition.

Still another lubricating composition of the present invention comprises the seal-compatible dispersant described herein combined with a dispersant-VI improver. The amount of the dispersant-VI improver can be from about 0.01 to about 15%, and preferably from about 0.5 to about 12.5% by weight of the composition.

The lubricating compositions of the present invention, in addition to the seal-compatible dispersant, the phenate detergent and the dispersant-VI improver, can also contain from about 50 to 1000, and preferably about 80 to about 400, ppm boron. The boron can be incorporated in the lubricating composition by post-treating the seal-compatible dispersant, or any dispersant used in combination therewith, with a boron-containing compound such as boric acid, such that the dispersant (including diluent) contains about 0.01 to about 5 wt. % boron and preferably about 0.1 to about 1.0 wt. % boron, and most preferably about 0.2 to about 0.7 wt. % boron.

When used in a concentrated form suitable for blending with lubricating oil to obtain a finished lube oil, the dispersant of the present invention can be in the form of a concentrate comprising about 20 to 90 wt. % inert organic diluent and about 10 to 80 wt. % of the dispersant of the present invention. As is conventional in the art, one or more other additives intended for the final lubricant can be included in the concentrate.

In somewhat greater detail, with respect to preparation of the seal-compatible dispersant of the present invention, the long chain hydrocarbyl-substituted succinic anhydride can be prepared by the alkylation of maleic acid or anhydride with the homopolymers and interpolymers of polymerizable olefin monomers containing up to about 10 carbon atoms, for example ethylene, propylene, 1-butene, 2-butene, isobutene, 1-hexene, or 1-octene, such polymers having at least about 40 and preferably at least about 50 carbon atoms in a chain in order to provide oil solubility to the dispersant of the invention. Typically the chain of carbons in the hydrocarbyl substituent ranges from about 40 to about 250, and preferably about 60–160. In general, the polymeric hydrocarbyl substituent should contain at least about 80 percent, and preferably about 95%, on a weight basis of units derived from aliphatic mono-olefins to preserve oil solubility. Especially suitable mono-olefins are isobutene and propene. The preferred hydrocarbyl substituent is polybutene or polypropene having number average molecular weight ($M_n$) of from about 250 to about 5,000. Particularly preferred is polybutene having a number average molecular weight ($M_n$) of about 750 to about 2500, and having ratio of weight average molecular weight ($M_w$) to number average molecular weight ($M_n$) of between 1.1 and 4.0.

Although it is preferred to react the above-described olefin polymer with maleic acid or anhydride, other unsaturated acids (or anhydrides) are contemplated, for example, acrylic acid, methacrylic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid, 2-pentene-1,3,5-tricarboxylic acid, and the like, including halogen-substituted carboxylic acid or derivatives thereof.

The reaction of the olefin polymer with maleic anhydride can be carried out in a conventional manner well known in the art using thermal or chlorination conditions. See, e.g., U.S. Pat. Nos. 3,215,707; 3,231,587; 4,234,435; European Patent Nos. 264,247 and 308,560 (chlorination) and Cengel U.S. Pat. Nos. 3,927,041; 3,935,249; 3,953,475; 3,954,812; 3,960,900; 3,985,672; 4,008,168; and 4,086,251 (thermal). All of these patents are hereby incorporated by reference. The ratio of anhydride groups to polybutene groups (SA:PIB ratio) in the polybutenyl succinic anhydride can be adjusted in the manner described in the '435, '247 and '560 patents, cited above to obtain SA:PIB ratios between about 0.5 and 4.0.

In accordance with the present invention, the hydrocarbyl-substituted succinic anhydride described above, preferably polybutenyl succinic anhydride ("PSA"), is reacted with aminoguanidine at a temperature of from about 155° C. to about 200° C. and preferably from about 170° to about 190° C. for a period of about 1 to about 5 hours, the ratio of reactants being about 1.4 to about 2.2 moles of aminoguanidine per equivalent of PSA. It is preferred to use a basic salt of aminoguanidine such as aminoguanidine bicarbonate. The preferred reaction conditions are a temperature of about 170° to 190° C., a ratio of 1.7 to 2.0 moles of aminoguanidine bicarbonate per equivalent of PSA, and a reaction time of about 2-4 hours.

The reaction temperatures prescribed above constitute a critical feature of the present invention. Reaction temperatures at or below about 155° C. result in a product which, although effective as a dispersant, elicits poor and generally unacceptable compatibility with fluorohydrocarbon-containing engine seals. Moreover, as the reaction temperature is reduced from about 155° C., seal compatibility worsens until : minimum in such performance is reached at a reaction temperature of about 130°-140° C. However, the trend observed when reaction temperatures above 155° C. are used is just the opposite. At about 155°-160° C., seal compatibility is borderline pass/fail. At reaction temperatures between 165° and 190° C., passing engine seal compatibility is obtained with a gradual improvement until a maximum in compatibility is achieved at about 185°-190° C.

Infrared analysis of PSA/aminoguanidine reaction product samples prepared at 130°, 145°, 150°, 155°, 160°, 170° and 185° C. discloses that greater than about 50% of the product obtained between 130° and 145° C. is a bis-amide having the following structure:

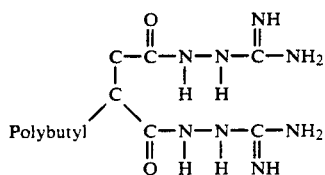

The bis amide has a characteristic IR absorbance at 1680 cm⁻¹. However, using a reaction temperature of between 145° and 185° C., the product is at least about 50% bis-3-amino-1,2,4-triazole having the following structure and tautomers thereof:

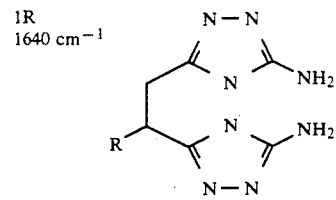

Infrared analysis further discloses that above reaction temperatures of about 160° C. the PSA/aminoguanidine reaction product is greater than about 90 wt. % triazole with very little if any detectable bis-amide, while at temperatures above about 165° C. the reaction product is essentially completely triazole.

Another important feature of the present invention is the ratio of aminoguanidine to PSA used in the preparation of the seal-compatible dispersant. The ratio is about 1.4 to 2.2 and preferably about 1.7 to 2.0 moles of aminoguanidine per equivalent of PSA. At ratios less than about 1.4 the reaction product shows increasingly poor dispersancy when compared with an equal amount of a conventional dispersant such as the Mannich product obtained by reacting polybutylphenol, formaldehyde, and a polyalkylene polyamine.

For purposes of the present invention, the weight of one equivalent of PSA is to be calculated on the basis that the equivalent weight of the PSA is based on the number of anhydride groups. This is to be distinguished from the convention used, for example, in U.S. Pat. No. 4,234,435 (column 28, lines 10 to 34) in which the number of equivalents of PSA depends on the number of carboxylic or acid-producing functions in the PSA. Therefore, because there are two carboxylic functions for each anhydride group of the PSA, the weight of one equivalent of PSA using the convention adopted in the present invention would be twice that obtained using the approach of the '435 patent. Conventional titration methods are readily available for determining the equivalent weight of a given sample of PSA. Generally speaking, preferred titration techniques are those which have reliable, easily ascertained titration end points and which detect the greatest amount of saponifiable anhydride in the PSA intermediate.

The aminoguanidine compound used to prepare the dispersant of the present invention is preferably a basic salt of aminoguanidine. The most preferred salt is aminoguanidine bicarbonate which can be obtained from commercial suppliers such as Nippon Carbide Industries, Inc.

Preparation of the dispersant of the present invention can be carried out in 100 neutral base oil using PSA that is generally about 45 to 85% "active" meaning that about 45 to 85% of the PSA composition is actual PSA, the remainder being principally unreacted polybutene and trace amounts of free maleic anhydride. Thus the dispersant composition, in practice, is a solution of the neat dispersant compound in a substantially inert carrier diluent consisting mainly of neutral base oil and unreacted polybutene. The wt. % of actual dispersant in this compound (i.e., the "activity") is preferably between about 35% and 60% and depends both on the PSA activity and the amount of neutral diluent oil used in the preparation of (or added to) the dispersant.

Because the PSA/aminoguanidine reaction product of the present invention is an excellent dispersant that is very compatible with fluorohydrocarbon-containing engine seals, it can be used as the sole dispersant in a lubricant formulation. However, it may also be used in combination with other well-known dispersants to obtain a dispersant combination that is compatible with engine seals. For example, if a formula containing a required level of a nitrogen-containing dispersant fails tests for engine seal compatibility, or elicits poor or marginal compatibility, it may be desirable to replace only so much of the conventional dispersant with the dispersant of the present invention as is necessary to render the formulation compatible with engine seals. Accordingly, one embodiment of the present invention is a composition suitable as a dispersing agent for lubricating oils, wherein the composition comprises a mixture of dispersant compounds having nitrogen-containing groups, said mixture comprising (a) at least one dispersant compound which is incompatible with fluorohydrocarbon-containing engine seals or which elicits poor or marginal compatibility with such seals and (b) a dispersant compound obtained by reacting a a hydrocarbyl substituted dicarboxylic compound selected from the group consisting of hydrocarbyl substituted dicarboxylic acids, hydrocarbyl substituted dicarboxylic acid anhydrides, and mixtures thereof, said hydrocarbyl substituent being about $C_{30}$–$C_{250}$, with aminoguanidine or a basic salt thereof, at a reaction temperature of from about 155° C. to about 200° C. and in a ratio of about 1.4 to about 2.2 moles of aminoguanidine or basic salt thereof per equivalent of hydrocarbyl substituted dicarboxylic compound, wherein the relative amounts of (a) and (b) in the mixture are such that the composition is compatible with fluorohydrocarbon elastomer engine seals.

Any nitrogen-containing dispersant can be used in combination with the triazole dispersant of the present invention. Examples (without limitation) are the succinimide dispersants (see, e.g., U.S. Pat. No. 4,234,435), the Mannich base dispersants (see U.S. Pat. No. 3,704,308) and the succinate ester-amide dispersants (see, e.g., U.S. Pat. No. 4,426,305). The patents cited are incorporated by reference. The additional dispersant can be borated or non-borated.

There are a number of different industry accepted tests for measuring the engine seal compatibility of lubricant formulations. Typically, these tests involve immersion of the seal in a fully formulated lubricant composition at an elevated temperature for a specified period of time, after which the seal material is examined for cracks, loss of elasticity, and loss of tensile strength. Because the tests vary in severity, the term "incompatible" or "incompatibility" as used in the present invention to characterize a dispersant should be understood to mean that the dispersant, when present in a fully formulated oil at the minimum concentration of dispersant necessary to meet dispersancy specifications required by the customer to whom the formulation is intended to be sold, is unable to pass the engine seal compatibility test required by that customer.

The present invention is also directed to lubricating compositions in which are combined the seal-compatible triazole dispersant disclosed herein and an alkaline earth metal phenate detergent. The neutral or overbased phenate detergents intended for use herein are exceedingly well known in the art. See, e.g., U.S. Pat. Nos. 3,493,516; 3,336,224; 4,412,927; 4,293,431; 4,464,289; 4,514,313; 3,718,589; 3,755,170; 4,302,342; 4,196,089, 4,293,431, etc., which are incorporated by reference. Briefly, the phenates for use in this invention are the alkaline earth metal, preferably magnesium or calcium, salts of alkylated phenols. The alkyl substituent(s) of the phenol (preferably para substituents) can contain from 3 to 200 carbons and preferably about 4 to 30 carbons. One of the functions of the phenates is to act as a detergent/dispersant. Among other things it prevents the deposit of contaminants formed during high temperature operation of the engine. The phenols can be mono- or polyalkylated.

The alkyl portion of the alkyl phenate lends oil solubility to the phenate, and can be obtained from naturally occurring or synthetic sources. Naturally occurring sources include petroleum hydrocarbons such as white oil and wax. If derived from petroleum, the hydrocarbon substituent is a mixture of different hydrocarbyl groups, the specific composition of which depends upon the particular oil stock which was used as a starting material. Suitable synthetic sources include various commercially available alkanes and alkane derivatives which, when reacted with the phenol, yield an alkylphenol. Suitable radicals obtained include butyl, hexyl, acetyl, decyl, dodecyl, hexadecyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefinic unsaturation). Generally, when the phenol is monoalkyl-substituted, the alkyl radical should contain at least 8 carbon atoms. The phenate may be sulfurized if desired. It can be either neutral or overbased and, if overbased, will have a base number of from about 150 up to 300 or more. Mixtures of neutral and overbased phenates may be used.

The phenates are ordinarily present in the oil to provide from about 0.2% to about 27% by weight of the total composition. Preferably, the neutral phenates are present from about 0.2% to about 9% by weight of the total composition, while the overbased phenates can be present from about 0.2% to 13% by weight of the total composition. Most preferably, the overbased phenates are present from 0.2% to 8% by weight of the total composition.

The sulfurized alkaline earth metal alkyl phenates are preferred, and can be obtained by a variety of processes such as treating the neutralization product of an alkaline earth metal base and an alkylphenol with sulfur. Conveniently, the sulfur, in elemental form, is added to the neutralization product and reacted at elevated temperatures to produce the sulfurized alkaline earth metal alkylphenate. Preferably, the sulfurization is carried out using ethylene glycol as a promoter. The preferred overbased phenates for use in the present invention are calcium sulfurized phenates having a total base number ("TBN") of about 150–400.

If more alkaline earth metal base is added during the neutralization reaction than is necessary to neutralize the phenol, a basic or "overbased" sulfurized alkaline earth metal alkyl phenate is obtained. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol. Carbon dioxide is the most commonly used material to produce the overbased phenates.

The present invention is also directed to lubricating compositions in which the seal-compatible dispersant described herein is combined with a dispersant-VI improver. Any dispersant-VI improver can be used. Examples are:

(a) polymers comprised of $C_4$ to $C_{24}$ unsaturated esters of vinyl alcohol or $C_3$ to $C_{10}$ unsaturated mono- or di-carboxylic acid with unsaturated nitrogen-containing monomers having 4 to 20 carbons;

(b) polymers of $C_2$ to $C_{20}$ olefin with unsaturated $C_3$ to $C_{10}$ mono- or di-carboxylic acid neutralized with amine, hydroxy amine, or alcohols;

(c) polymers of ethylene with a $C_3$ to $C_{20}$ olefin further reacted either by grafting $C_4$ to $C_{20}$ unsaturated nitrogen-containing monomers thereon or by grafting an unsaturated acid onto the polymer backbone and then reacting said carboxylic acid groups with amine, hydroxy amine, or alcohol; and (d) polymers of ethylene and a $C_3$ to $C_{20}$ olefin further reacted first with oxygen and subsequently with formaldehyde and an amine.

It is preferred that the viscosity index improver dispersant have a number average molecular weight range of 1,000 to 2,000,000, preferably 5,000 to 250,000, and most preferably 10,000 to 200,000.

Typical polymeric viscosity index improver dispersants include copolymers of alkyl methacrylates with N-vinyl pyrrolidone or dimethylaminoalkyl methacrylate, alkyl fumarate-vinyl acetate, N-vinyl pyrrolidone copolymers, post-grafted interpolymers of ethylene-propylene with an active monomer such as maleic anhydride which may be further reacted with an alcohol or an alkylene polyamine, e.g , see U.S. Pat. Nos. 4,059,794, 4,160,739, and 4,137,185; or copolymers of ethylene and propylene reacted or grafted with nitrogen compounds such as shown in U.S. Pat. Nos. 4,068,045, 4,063,058, 4,146,439, and 4,149,984; and styrene/maleic anhydride polymers post-reacted with alcohols and amines, ethoxylated derivatives of acrylate polymers, for example, see U.S. Pat. No. 3,702,300.

A preferred polymeric dispersant-VI improver suitable for use in the present invention is that of category (d) above, i.e., the Mannich reaction product of an oxidized ethylene-propylene copolymer, an amine, and a formaldehyde yielding reagent. Commonly assigned U.S. Pat. Nos. 3,864,268; 3,872,019; 4,011,380; 4,131,553; 4,170,562; and 4,444,956 (all of which are incorporated by reference herein) disclose the preparation of such Mannich dispersant-VI improvers.

Among the several embodiments of the present invention are fully formulated lubricating compositions comprising a major amount of an oil of lubricating viscosity and a minor effective dispersant amount of the triazole dispersant described above, as well as lubricating compositions in which the triazole dispersant is used in combination with the above-mentioned phenate detergents and/or the above-described dispersant-VI improvers.

The oil of lubricating viscosity for use in the lubricating compositions of the present invention can be natural or synthetic in origin or mixtures thereof. The lubricating compositions of the invention can be used in crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants, hydraulic fluids and other lubricating oil and grease compositions can also benefit from the incorporation therein of the lubricating compositions of the present invention.

With respect to the oil constituting the major portion of the lubricating compositions of the present invention, suitable natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins (e.g., polybutylenes, polypropylenes, polylene-isobutylene copolymers, chlorinated polybutylenes, etc.); poly(1-hexenes), poly(1-octenes), poly(1-decenes), etc., and mixtures thereof; alkylbenzenes (e.g., dodecylbenzenes, tetradecylbenzenes, dinonylbenzenes, di(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500 to 1000, diethyl ether of polypropylene glycol having a molecular weight of 1000 to 1500, etc.) or mono- and polycarboxylic esters thereof, for example, the acetic acid esters, mixed $C_3$–$C_8$ fatty acid esters, or the $C_{13}$ oxo acid diester of tetraethylene glycol.

Another suitable class of synthetic lubricating oils comprises the esters of dicarboxylic acids (e.g., phthalic acid, succinic acid, alkyl succinic acid, and alkenyl succinic acids, maleic acid, azelaic acid, suberic acid, sebacic acid, fumaric acid, adipic acid, linoleic acid dimer, malonic acid, alkyl malonic acids, alkenyl malenic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-outylpheny) silicate, hexa-(4-methyl-2-pentoxy)-disiloxane, poly(methyl)siloxanes, poly(methylpheny)siloxanes, etc.). Other synthetic lubricating oils include liquid esters of phosphorus-containing acids (e.g., tricresyl phosphate, trioctyl phosphate, diethyl ester of decylphosphonic acid, etc.) polymeric tetrahydrofurans and the like.

Unrefined, refined and rerefined oils, either natural or synthetic (as well as mixtures of two or more of any of these) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

The present invention is further directed to so-called "additive packages" or additive concentrates incorporating the triazole dispersant of the present invention, preferably in combination with a phenate detergent. In the manufacture of fully formulated lubricants containing numerous specialized additives, it is common to introduce the additives in the form of concentrates in hydrocarbon solvent, for example, mineral lubricating oil or other suitable substantially inert organic solvent/diluent. The concentrates normally contain about 20 to 80 wt. % active additive ingredients. The additive concentrate is then blended with about 3 to 40 parts by weight lubricating oil per part by weight of the additive concentrate to obtain the finished lubricating oil. The use of concentrates facilitates shipping and final blending of the lubricant additives.

The seal-compatible dispersant composition of the present invention can be post-treated in a well-known manner with a boron-containing compound in order to introduce from about 0.01 to about 5 wt. % boron into the dispersant. A preferred amount of boron is about 0.1 to about 1.0 wt. %. Particularly preferred is about 0.2 to about 0.8 wt. % boron. While the boron acts as a corrosion inhibitor, it can also improve even further the compatibility of the dispersant toward fluorohydrocarbon engine seals. Suitable boron-containing compounds for post-treatment of the dispersant of the present invention include, without limitation, polyborate esters, boron acids, boron oxides, boron halides, esters of boron acids, and salts of boron acids. The use of boron-containing compounds in modifying dispersants is described in more detail in the following patents which are hereby incorporated by reference: U.S. Pat. Nos. 3,344,069; 4,080,303; 3,087,936; 3,254,025; 3,322,670; 4,426,305; European Patent Application No. 83301723.9 (Publication No. 0,090,629) and No. 84304928.9 (Publication No. 0,132,383).

In those instances in which the dispersant of the present invention has been post-treated with boron and incorporated into a finished lubricating composition, the resulting level of boron present in the composition can be anywhere from about 50 to about 1000 ppm and is preferably from about 80 to about 400 ppm.

Briefly, a boron-containing reagent useful in borating the seal-compatible dispersant of the present invention can be prepared as follows: Charge 309 grams boric acid, 185 grams toluene, and 370 grams isobutyl alcohol to a reaction vessel. Blanket with nitrogen and heat to 200°-230° F. Collect the water produced in the reaction and reflux the toluene and alcohol back to the reaction. Increase the temperatures to 260°-280° F. and strip with nitrogen until all the toluene is removed. Cool to 240° F. and filter. The boron content of the resulting product is 8.4%. Amylpolyborate can be prepared as follows: Charge 309 grams of boric acid, 185 grams toluene and 440 grams amyl alcohol. Blanket with nitrogen and heat to 200°-230° F. Collect the water and reflux the toluene and alcohol back to the reactor. Increase the temperature to 260° to 280° F. and strip with nitrogen until all the toluene is removed. The resulting borate ester material has a boron content of about 8.5 to 8.9%.

Finally, it is contemplated that the dispersant of the present invention, as well as the combination thereof with phenates and dispersant-VI improvers, can be used in lubricant compositions containing other conventional additives. A brief survey of conventional additives for lubricating compositions is contained in the publications, LUBRICANT ADDITIVES, by C. V. Smalheer and R. Kennedy Smith, published by Lezuis-Hiles Co., Cleveland, Ohio (1967) and LUBRICANT ADDITIVES, by M. W. Ranney, published by Noyes Data Corp., Park Ridge, N.J. (1973). These publications are incorporated herein by reference.

Conventional additives include oxidation inhibitors such as zinc dithiophosphates, hindered phenols, aromatic amines, sulfurized phenols, and oil-soluble copper salts (e.g., copper carboxylate); dispersants, such as high molecular weight alkyl succinimides, alkylthiophosphonates and the like, and Mannich base dispersants; metal deactivators such as zinc dithiophosphates, organic sulfides, and certain organic nitrogen compounds; anti-wear agents such as zinc dithiophosphates organic phosphates and acid phosphates, organic sulfur compounds, sulfurized fats and amines; rust inhibitors, such as metal sulfonates, fatty acids and amines; corrosion inhibitors such as zinc dithiophosphates and basic metal sulfonates; foam inhibitors such as silicone polymers and friction modifiers such as fatty acids and amides, glycerol monooleate, pentaerythritol monooleate, sorbitan monooleate (including borated or sulfurized products of these partial esters), lard oil, sperm oil, high molecular weight organic phosphorus acids and esters.

The following examples are for the purpose of illustration only and are not intended to limit the scope of the present invention.

EXAMPLE 1

A polybutenyl-bis-3-amino-1,2,4-triazole dispersant in accordance with the present invention was prepared as follows. Into a three-liter, three-necked, round-bottom flask, 1000 gm of 57.5% active polybutenyl succinic anhydride having an equivalent weight of 1950 (0.29 equivalents), 69.9 gm of 98.5% aminoguanidine bicarbonate (0.50 mole), and 494 gm of a 100 neutral base oil were placed under nitrogen. The polybutenyl succinic anhydride had been prepared by reacting maleic anhydride with polybutene having a number average molecular weight ($M_n$) of about 2100. The mixture, under constant stirring, was heated for three hours at a temperature of 188° C. (370° F.) to form the polybutenyl bis-3-amino-1,2,4-triazole. The product was filtered to provide a 40% active polybutenyl bis-3-amino-1,2,4-triazole dispersant, identified hereinafter as Dispersant No. 1.

In a similar manner, a second embodiment of the dispersant of the present invention was prepared. In this preparation, the polybutenyl succinic anhydride was prepared by reacting maleic anhydride with polybutene having $M_n$ of about 1250. This polybutenyl bis-3-amino-1,2,4-triazole dispersant is identified hereinafter as Dispersant No. 2.

Each of these two dispersants was tested in both the spot dispersancy test (SDT) and the oil thickening spot dispersancy test [OTT(SDT)]. Each of these tests measures the ability of a dispersant to suspend and move sludge chromatographically along blotter paper. For comparison, a typical commercial Mannich base dispersant, identified hereinafter as Dispersant No. 3, was also subjected to these tests. The results of these tests are presented hereinbelow in Table I.

TABLE I

| | Dispersant Performance | | | | | | | |
|---|---|---|---|---|---|---|---|---|
| | SDT % | | | | OTT (SDT) Time, hr | | | |
| Dispersant | 0 | 2 | 4 | 6 | 24 | 48 | 56 | 72 |
| 1 | 37 | 46 | 85 | 84 | 100 | 93 | 90 | 42 |
| 2 | 37 | 58 | 85 | 86 | 100 | 90 | 75 | 34 |
| 3 | 37 | 60 | 84 | 88 | 100 | 88 | 69 | 28 |

These results indicate that the two embodiments of the dispersant of the present invention perform in the SDT and OTT in a manner similar to that of the reference Mannich dispersant.

EXAMPLE 2

A polybutenyl bis-3-amino-1,2,4-triazole dispersant was prepared using the preparation of Example 1, and a polybutenyl succinic anhydride (PSA) in which the ratio of succinic groups to polybutene groups (SA:PIB ratio) in the active portion of the PSA (excluding unreacted polybutene) was between 2.5 and 3.5 using the following formula to calculate such ratio:

$$SA:PIB = \frac{PIB\ (M_n)}{Eq.\ wt. - 98}$$

in which PIB($M_n$) is the number average molecular weight of the starting polybutene used to prepare the PSA and "Eq. wt." is the equivalent weight of the PSA.

EXAMPLE 3

Example 2 was repeated using PSA having an SA:PIB ratio of 2.0 to 2.5.

EXAMPLE 4

Example 2 was repeated using PSA having an SA:PIB ratio of 1.5 to 2.0.

EXAMPLE 5

Example 2 was repeated using PSA having an SA:PIB ratio of 1.0 to 1.5.

EXAMPLE 6

In this example, two embodiments of the dispersant of the present invention were tested for their compatibility with Viton ® fluorohydrocarbon elastomers. Viton ® fluorohydrocarbon elastomers are used as crankshaft seals in engines and clutch plate liners in transmissions.

Caterpillar Tractor Company of Peoria, Ill., U.S.A., has developed an experimental test for evaluating the compatibility of such elastomers and an oil containing a dispersant. According to this test, three elastomer specimens are submersed in a candidate oil for ten days at a temperature of 149° C. (300° F.). The average percent elongation measurement represents a loss of flexibility of the Viton ® material. A lower value indicates a more flexible material which has resisted attack by the oil. The higher the value, the less flexible the sample. Caterpillar has established a passing oil and a failing oil to be used as references or standards for discriminating between and evaluating the candidate oils.

A conventional SF/CD heavy duty oil, identified hereinafter as Oil No. 1, was used in these tests. The dispersants were tested at a 5.5 wt. % level. This oil contained Paratone 715, a non-dispersant VI improver, obtained from Paramins, a division of Exxon Corporation, in an amount of 6.9 wt. %. The heavy duty oil, Oil No. 1, was tested without dispersants to demonstrate its contribution to incompatibility.

Both the Caterpillar passing oil, identified hereinafter as Oil No. 2, and the Caterpillar failing oil, identified hereinafter as Oil No. 3, were tested for their compatibility with the Viton ® elastomers.

In addition, two oil samples contained a third embodiment of the dispersant of the present invention, Dispersant No. 4, which third embodiment was prepared in accordance with Example 1 from PSA made from polybutene having a $M_n$ of about 1250 and two oil samples contained a fourth embodiment of the dispersant of the present invention, Dispersant No. 5, which fourth embodiment was prepared according to Example 1 from PSA made from polybutene having $M_n$ of about 2100. Two of these latter four samples also contained boron in the form of 0.45 wt. % amylpolyborate. Each of the samples involving Oil No. 1 contained 6.9 wt. % VI improver Paratone 715, obtained from Paramins, a division of Exxon Corporation.

The results of these tests are presented in Table II hereinbelow.

TABLE II

| | Caterpillar Viton ® Compatibility Tests | | |
|---|---|---|---|
| Oil No. | Dispersant, 5.5 wt. % | Amylpolyporate, wt. % | % Elongation |
| 1 | — | — | 12 |
| 1 | — | — | 12 |
| 2 | — | — | 25 |
| 3 | — | — | 46 |
| 1 | 4 | — | 26 |
| 1 | 4 | 0.45 | 20 |
| 1 | 5 | — | 22 |
| 1 | 5 | 0.45 | 16 |

These data demonstrate that both Dispersant No. 4 and Dispersant No. 5 provided % elongations that were quite similar to that furnished by the Caterpillar passing oil reference, Oil No. 2. The addition of boron resulted in an improvement in the % elongation, i.e., a reduction in the % elongation. Consequently, either Dispersant No. 4 or Dispersant No. 5 shows good compatibility with Viton ® seals in the Caterpillar test, with or without boron.

EXAMPLE 7

In this example samples of dispersants were prepared by reacting polybutenyl succinic anhydride with either aminoguanidine bicarbonate (AGB), obtained from Aldrich Chemical Co., or aminoguanidine nitrate (AGN), obtained from Aldrich Chemical Co. or aminoguanidine hemisulfate (AGH), obtained from Eastman Kodak Co. The preparations of the polybutenyl succinic anhydrides and the resulting dispersant products were conducted as described hereinabove. The polybutenyl succinic anhydrides were either PSA-1, which were prepared from polybutene having $M_n$ of about 1290, or PSA-2, which were prepared from polybutene having $M_n$ of about 2060. Dispersant products were obtained by reacting one mole of PSA-1 with one mole of AGB (Dispersant No. 6), one mole of PSA-1 with two moles of AGN (Dispersant No. 7), one mole of PSA-1 with PSA-1 with two moles of AGH (Dispersant No.-8), one mole of PSA-1 with two moles of AGM (Dispersant No. 9), one mole of PSA-2 with one mole of AGB (Dispersant No. 10), and one mole of PSA-2 with two moles of AGB (Dispersant No. 11). A typical Mannich base dispersant (Dispersant No. 12) was used as a reference.

Each of the resulting dispersant products was subjected to the spot dispersancy test (SDT) and to the oil thickening test (OTT). The spot dispersancy test measures the movement of insoluble particles chromatographically along blotter paper in used motor oil. When a dispersant candidate is used, oil movement along the paper results in two rings. The inner ring constitutes the sludge being transported by the dispersant; the outer ring comprises the base oil. The effectiveness of the dispersant is defined by the ratio of the inner ring to the outer ring. The higher the value of this ratio for a particular candidate, the better the performance of that candidate as a dispersant. The oil thickening test is an analogous test in which the dispersant is tested in an oil that is being oxidized and the spot dispersancy test indicates the effect of this oxidation with time.

The results of the spot dispersancy tests are presented hereinbelow in Table III. The results of the oil thickening tests are presented hereinbelow in Table IV.

The results presented in Table III show that a product prepared with one mole of aminoguanidine bicarbonate per mole of PSA, or a product prepared with two moles of aminoguanidine nitrate per mole of PSA, or a product prepared with two moles of aminoguanidine hemisulfate per mole of PSA does not provide a response equivalent to that of Dispersant No. 12, the typical Manrich base dispersant. The use of two moles of aminoguanidine bicarbonate per mole of PSA when using either type of PSA did give a response that is equivalent to the response provided by the reference Mannich base dispersant. In addition, there was no great distinction between responses provided by the bistriazole products prepared from either PSA at equal weight.

The results presented in Table IV demonstrate that the products prepared from either one mole or two moles of aminoganidine bicarbonate per mole of PSA furnished OTT responses that were not appreciably different from the response provided by the reference Mannich base dispersant. Hence the oxidation of these products is similar to that of the reference Mannich base dispersant.

EXAMPLE 8

In this example, samples of products were prepared from aminoguanidine bicarbonate obtained from two sources. Some were prepared from aminoguanidine bicarbonate obtained from Aldrich Chemical Company. This material was 98.5% pure. Other samples were prepared from aminoguanidine bicarbonate obtained from Nippon Carbide Industries Co., Inc. This material was either 99.7% or 92.9% pure amine. Reactions were conducted with each of the three specimens of aminoguanidine bicarbonate at AGB:PSA ratios of 1.9:1 or 1:1 for both PSA-1 and PSA-2. The 92.9% aminoguanidine bicarbonate, which contained approximately 7% water caused a great deal more foaming during the reaction than the others. Nitrogen content (Dumas) and viscosity were determined for each product. Spot dispersancy tests were conducted for each dispersant product. The Mannich dispersant was used again as a reference. The results of these tests are presented hereinafter in Table V.

TABLE III

| Dispersant Product No. | PSA-1 Type | AG Salt (1) Moles | AG Salt (1) Type | Wt. % Dispersant 0 | 2 | 4 | 6 |
|---|---|---|---|---|---|---|---|
| 6 | PSA-1 | 1 | AGB | 35 | 43 | 58 | 71 |
| 7 | PSA-1 | 2 | AGN | 35 | 39 | 43 | 63 |
| 8 | PSA-1 | 2 | AGH | 35 | 39 | 41 | 55 |
| 9 | PSA-1 | 2 | AGB | 35 | 49 | 84 | 92 |
| 10 | PSA-2 | 1 | AGB | 35 | 42 | 46 | 66 |
| 11 | PSA-2 | 2 | AGB | 35 | 56 | 82 | 87 |
| 12 | — | — | — | 35 | 54 | 76 | 88 |

(1) AG Salt = aminoguanidine salt.

TABLE IV

| Dispersant Product No. | PSA-1 Type | AG Salt (1) Moles | AG Salt (1) Type | Time, hr 24 | 48 | 56 | 72 | 80 |
|---|---|---|---|---|---|---|---|---|
| 6 | PSA-1 | 1 | AGB | 100 | 85 | 73 | 71 | — |
| 9 | PSA-1 | 2 | AGB | 100 | 90 | 75 | 34 | — |
| 10 | PSA-2 | 1 | AGB | 100 | 89 | 87 | 47 | 41 |
| 11 | PSA-2 | 2 | AGB | 100 | 93 | 90 | 42 | — |
| 12 | — | — | — | 100 | 89 | 69 | 28 | 30 |

(1) AG Salt = aminoguanidine salt.

TABLE V

Effect of AGB Source and Amount on SDT

| PSA Type | AGB Source | AGB Purity, % | AGB:PSA | Viscosity, cSt |
|---|---|---|---|---|
| PSA-1 | A[1] | 98.5 | 1:1 | 183 |
| PSA-1 | N[2] | 99.7 | 1:1 | 176 |
| PSA-1 | N | 92.9 | 1 1 | 176 |
| PSA-1 | A | 98.5 | 1.9:1 | 190 |
| PSA-1 | N | 99.7 | 1.9:1 | 205 |
| PSA-1 | N | 92.9 | 1.9:1 | 185 |
| PSA-2 | A | 98.5 | 1:1 | 454 |
| PSA-2 | N | 99.7 | 1:1 | 480 |
| PSA-2 | N | 92.9 | 1:1 | 463 |
| PSA-2 | A | 98.5 | 1.9:1 | 516 |
| PSA-2 | N | 99.7 | 1.9:1 | 536 |
| PSA-2 | N | 92.9 | 1.9:1 | 490 |
| MANNICH DISPERSANT | — | — | — | — |

| PSA Type | N, % | SDT wt. % Dispersant 0 | 2 | 4 | 6 |
|---|---|---|---|---|---|
| PSA-1 | 1.97 | 39 | 39 | 60 | 72 |
| PSA-1 | 1.99 | 39 | 40 | 59 | 71 |
| PSA-1 | 1.87 | 39 | 40 | 63 | 71 |
| PSA-1 | 2.97 | 39 | 55 | 76 | 79 |
| PSA-1 | 2.98 | 39 | 61 | 72 | 80 |

TABLE V-continued
Effect of AGB Source and Amount on SDT

| PSA-1 | 3.06 | 39 | 55 | 76 | 83 |
|---|---|---|---|---|---|
| PSA-2 | 0.98 | 39 | 45 | 44 | 60 |
| PSA-2 | 1.19 | 39 | 40 | 47 | 67 |
| PSA-2 | 1.02 | 39 | 37 | 51 | 73 |
| PSA-2 | 1.95 | 39 | 59 | 74 | 78 |
| PSA-2 | 1.74 | 39 | 57 | 74 | 80 |
| PSA-2 | 1.94 | 39 | 62 | 77 | 80 |
| MANNICH | 1.15 | 39 | — | 79 | — |

[1]A = Aldrich Chemical Company
[2]N = Nippon Carbide Industries Co., Inc.

The data in this table suggest that the nitrogen content is consistent within each type of product. For example, the bis-triazole dispersants made with PSA-1 and at an AGB:PSA ratio of 1.9:1 have a nitrogen content of approximately 3% regardless of the source of aminoguanidine bicarbonate. The viscosities of the products are similar, varying with the molecular weight of PSA employed. For a particular molecular weight of PSA, the viscosities are slightly higher when a larger ratio of AGB to PSA is used. The spot dispersancy tests discriminated between the type of product prepared (AGB:PSA molar ratio); however, they did not show any appreciable differences in the products obtained from AGB's having different sources. In addition, infrared spectra obtained on the dispersants prepared from PSA-1 showed very little differences, suggesting that the same product was being prepared regardless of the source of AGB.

EXAMPLE 9

In this example, the friction modification properties of an embodiment of the dispersant of the present invention were evaluated. The embodiment was prepared by reacting PSA-1 with AGB as described hereinabove. This embodiment is identified hereinafter as Dispersant No. 13. It was compared with a typical Mannich base dispersant, Dispersant No. 14.

Oils containing the dispersants were prepared to the same viscosities. Each oil sample was made up of a solvent-extracted, 20 weight, Gulf Canada base stock, Oil No. 4, 4.0 wt. % dispersant, 1.0 wt. % zinc dialkyldithiophosphate inhibitor, 1.2 wt. % high-base magnesium sulfonate rust inhibitor, and 0.08 wt. % copper carboxylate. These were SAE 20 straight grade oils.

The friction modification properties of each oil were evaluated in a motored engine test. The base line oil used in these tests was a 10W40 multigrade oil, "LDO," obtained from Amoco Oil Company. This base line oil was assigned arbitrarily a percent improvement of zero in the boundary friction area. The experimental oils were then measured as positive or negative in relation to "LDO" in the boundary friction area. The results of these motored engine tests are presented hereinbelow in Table VI.

TABLE VI
Motored Engine Tests

| Oil | Dispersant | Grade | Boundary Friction Area % Improvement |
|---|---|---|---|
| LDO | — | 10W40 | 0 |
| 4 | 13 | 20 | −20 to −40 |
| 4 | 14 | 20 | .9 |

These results demonstrate that the oil containing the embodiment of the dispersant of the present invention provided a marked improvement in the boundary friction area of the motored engine over the oil containing the typical Mannich dispersant.

EXAMPLE 10

This example is a comparison of the present invention and Example 38 of U.S. Pat. No. 3,272,746, for the purpose of demonstrating the criticality of the reaction temperatures required herein for preparation of the polybutylbis-3-amino-1,2,4-triazole dispersant of the present invention. This criticality relates to the compatibility of the dispersant with fluorohydrocarbon elastomer engine seals.

Example 38 of the '746 patent (read in conjunction with Example 1 of that patent) calls for reaction of 1000 grams of polybutenyl succinic anhydride ("PSA") with 254 grams of aminoguanidine bicarbonate. Using the equivalent weight convention of the present invention wherein the equivalent of the PSA is based on the number of anhydride groups, the ratio of aminoguanidine bicarbonate to PSA in Example 38 of the '746 patent is about 1.9:1. A specific reaction temperature was not disclosed, only a range of 130° C.—165° C. The reaction time was 5 hours and the resulting dispersant was diluted to 50% activity with mineral oil.

Insofar as the prior art example disclosed only a range of reaction temperatures (130° C.-165° C.), the example was duplicated using seven different reaction temperatures, five of which being in the 130°-165° C. range prescribed by the prior art example. The seven reaction temperatures were: 130°, 145°, 150°, 155°, 160°, 170° and 185° C. Infrared analysis was carried out on the seven samples. The analysis disclosed the presence of two species in varying relative amounts depending upon the reaction temperature used. The two species were the bis-amide having a characteristic absorbance maximum at 1680 cm$^{-1}$ and the bis 1,2,4 triazole having a characteristic absorbance maximum at 1640 cm$^{-1}$. Quantitative IR analysis was carried out to determine the relative amount of triazole versus bis-amide for the seven reaction temperatures. Table A summarizes these analyses.

TABLE A

| Reaction Temperature | % Triazole (wt.) |
|---|---|
| 130° C. | 30–40% |
| 145° C. | 50–60% |
| 150° C. | 65–70% |
| 155° C. | 85–90% |
| 160° C. | 95–100% |
| 170° C. | ~100% |
| 185° C. | ~100% |

The IR spectral analysis shows the trend of bis-amide to bis-triazole as the reaction temperature is increased from 130° C. to 160° C.

To assess the performance of the products, five of the above samples were examined (130°, 145°, 160°, 170° and 185°) in the spot dispersancy and VW Viton ® tests. In the spot test, the candidate dispersant is mixed with used drain oil from a Sequence VE engine, and heated at 150° C. for 18 hours. Ten drops of the heated mixture is applied to chromatography paper and allowed to spread for 24 hours. With no dispersant, the coagulated sludge remains at the center of the spot and the oil forms a large ring. With a good dispersant, the complexed sludge is carried out into the ring along with the oil. In this test, all of the samples show good dispersancy, similar to a commercial dispersant used as a standard.

The VW Viton ® test is used to determine the compatibility of an oil-containing dispersant with fluorohydrocarbon elastomer seals. Rubber specimens are immersed in a beaker of the test oil and held at 150° C. for four days. The rubber then is rated for cracking, and change in tensile strength and elongation. In this test the two products which contain significant amounts of amide (130° C. and 145° C.) failed badly by all three criteria. The material prepared at 160° C. gave a borderline fail on change in elongation, while the materials prepared at the higher temperatures (170° and 185° C.) passed all three ratings. Based on these results, a clear advantage can be seen for the products containing at least a majority of triazole at temperatures above about 155° C. and preferably products containing essentially all triazole at temperatures above about 170° C.

The results of the VW Viton ® tests for the reaction product of two moles of aminoguanidine bicabonate per equivalent of PSA (derived from polybutene having $M_n$ of about 1300) at various reaction temperatures are set forth in Table B below.

TABLE B

| Preparation Temperature | Infrared[1] Analysis | VW Viton[3] Cracks | $\Delta$ E[2] | $\Delta$ TS[2] |
|---|---|---|---|---|
| 130° C. | A | MOD-HVY | −52 | −51 |
| 145° C. | A,T | Severe | −46 | −48 |
| 160° C. | T | None | −38 | −29 |
| 170° C. | T | None | −34 | −24 |
| 185° C. | T | None | −32 | −24 |

[1]A = amide 1680 cm$^{-1}$
[1]T = triazole 1640 cm$^{-1}$
[2]Elongation tensile strength
[3]Passing: cracks-very light or none
$\Delta$ E < 35
$\Delta$ TS < 45

EXAMPLE 11

The triazole dispersant of the present invention was tested in a fully formulated lubricating composition containing the dispersant at a treat amount sufficient to satisfy the stringent "SG" specifications. The formulation in the table below is a lubricating composition according to the present invention comprising 7.7 wt. % polybutenyl-bis-3-amino-1,2,4-triazole dispersant prepared from PSA of equivalent weight about 1950 in which the polybutene has $M_n$ of about 2100. The lubricating composition, among other additives, includes an overbased calcium sulfurized phenate. The formulation was tested in the "VE" test which measures dispersancy by rating average sludge ("AS") average varnish ("AV") and piston varnish ("PV") on a scale of 1 to 10, 10 being the best.

TABLE C

| VE Testing of Triazole Dispersant | |
|---|---|
| Component | Wt. % |
| Base Stocks VI Improver Overbased Sulfonate Pour Point Depressant Zinc Dialkyl-dithiophosphate | 75.4 |
| Overbased Calcium Sulfurized Phenate Oxidation Inhibitor SX-5 | 1.25 |
| Polybutenyl ($M_n$ 2100) bis-3-amino-1,2,4-triazole | 7.70 |

VE Engine Test Results

TABLE C-continued

| VE Testing of Triazole | |
|---|---|
| RACS | = 9.21 (passing is >7) |
| AS | = 9.42 (passing is >9) |
| AV | = 6.23 (passing is >5) |
| PV | = 6.89 (passing is >6.5) |
| Wear max | = 1.0 (passing is <15) |
| Wear avg | = .65 (passing is <5) |

Note:
"RACS" is Rocker Arm Cover Sludge
"AS" is average sludge
"AV" is average varnish
"PV" is piston varnish As can be seen from the VE engine test results, the lubricating composition of the present invention comprising the triazole dispersant in combination with overbased calcium sulfurized phenate provided excellent sludge and varnish cleanliness.

EXAMPLE 12

A lubricating composition according to the present invention was formulated to meet "CD" diesel engine specifications. The formulation and its performance in the Caterpillar 1-G2 engine test are shown below in Table D.

TABLE D

| CAT 1-G2 Testing of Lube Oil Containing Triazole Dispersant | |
|---|---|
| Component | Wt. % |
| Base Stocks | 80.81 |
| VI Improver | |
| Polybutenyl ($M_n$ 2100) bis-3-amino-1,2,4 Triazole Dispersant | 5.0 |
| Zinc Dialkyl-dithiophosphate | |
| Oxidation Inhibitor | |
| Overbased Calcium Sulfurized Phenate | 1.5 |
| Low Base Calcium Sulfonate | |
| High Base Magnesium Sulfonate | |
| High Base Calcium Sulfonate | |
| Polyborate | 0.19 |

| Cat. 1-G2 Test Results | | |
|---|---|---|
| | 240 Hours | 480 Hours |
| Top Groove Fill[1] | 49 | 49 |
| Weighted Carbon Demerits | 58 | 61 |
| Weighted Lacquer Demerits | 47 | 81 |
| Weighted Total Demerits[2] | 105 | 142 |

[1]Passing is <80
[2]Passing is <300

EXAMPLE 13

This example compares Viton ® the fluorohydrocarbon engine seal compatibility of the triazole dispersant of the present invention with two non-triazole dispersants containing nitrogen groups which are aggressive toward Viton ® engine seals. Non-triazole dispersant ("A") was a succinimide dispersant posttreated with boron and ("B") was a borated succinate ester-amide. The triazole dispersant of the present invention is "C." The formulation in which the comparison was done was an SG/CD formulation containing overbased calcium sulfurized phenate. The formulation was as follows:

TABLE E

| Component | Wt. % |
|---|---|
| Zinc Dialkyldithiophosphate | |
| High Base Magnesium Sulfonate | |
| High Base Calcium Sulfonate | |
| High Base Calcium Sulfurized Phenate | 1.25 |
| Oxidation Inhibitors | |
| Diluent | 0.10 |
| Base stocks | 80.2 |
| VI Improver (or dispersant-VI) | 8.3 |
| Dispersant A, B, or C | 7-9 |

Table F sets forth results of testing various concentrations of dispersants A, B, C in the above formulation in the VW Viton ® test. In the test, samples of the Viton ® fluorohydrocarbon rubber are immersed in the test oil and held at 150° C. for four days in an oven. The rubber specimens are removed from the oven and rated for cracking and changes in modulus, elongation and tensil strength.

TABLE F

| Dispersant | Wt. % | VW Viton ® Cracks[1] | $\Delta E^{[2]}$ | $\Delta TS^{[3]}$ |
|---|---|---|---|---|
| B | 7 | None | 23 | 31 |
| A[4] | 7 | None | 11 | 18 |
| A[4] | 8 | None | 28 | 30 |
| A[4] | 9 | Weak Cracks | 34 | 35 |
| A[5] | 6 | None | 32 | 37 |
| A[5] | 7 | Cracks | 38 | 41 |
| A[5] | 9 | Cracks | 41 | 42 |
| C[4] | 6 | None | 12 | 2.1 |
| C[4] | 7 | None | 14 | 6.4 |
| C[4] | 8 | None | 14 | 6.4 |
| C[5] | 4 | None | 20 | 11 |
| C[5] | 6 | None | 20 | 15 |
| C[5] | 8 | None | 22 | 18 |

Notes:
[1]Passing is no cracks.
[2]Passing is <35.
[3]Passing is <45.
[4]Formulation contained 8.3% non-dispersant-VI improver.
[5]Formulation contained 8.3% dispersant-VI improver (Mannich reaction product of olefin copolymer (EP), formaldehyde and alkylene diamine.)

The data in Table F demonstrates that, as dispersant treat rate is increased in the formulation of Table E, the formulation containing the non-triazole dispersant ("A") deteriorated markedly in terms of engine seal compatibility, and the problem was particularly evident in the formulation containing 8.3% of the dispersant-VI improver. In sharp contrast are the formulations containing the triazole dispersant ("C") of the present invention. Even at the highest level of dispersant, 8%, with 8.3% dispersant-VI improver in the formulation, the Viton ® engine seals held up very well.

We claim:

1. A method for preparing a dispersant composition having improved compatibility toward fluorocarbon containing elastomer engine seals which comprises: reacting a hydrocarbyl substituted dicarboxylic compound selected from the group consisting of hydrocarbyl substituted dicarboxylic acids, hydrocarbyl substituted dicarboxylic acid anhydrides, and mixtures thereof, said hydrocarbyl substituent being about $C_{20}$-$C_{250}$, with aminoguanidine or a basic salt thereof, at a reaction temperature of from about 170° C. to about 200° C. and in a ratio of about 1.4 to about 2.2 moles of aminoguanidine or basic salt thereof per equivalent of hydrocarbyl substituted dicarboxylic compound, to obtain a dispersant composition comprising, exclusive of diluent present, at least about 95 wt. % of a triazole compound having a characteristic infrared absorbance at 1640 cm$^{-1}$.

2. The method of claim 1 wherein the hydrocarbyl substituent is about $C_{60}$-$C_{200}$ polyalkenyl derived from $C_3$ or $C_4$ polymerizable olefins.

3. The method of claim 2 wherein the polyalkenyl substituent is polybutenyl.

4. The method of claim 3 wherein the polybutenyl substituted dicarboxylic compound is the reaction product of reactants comprising polybutene having $M_n$ of about 750 to about 2500 and maleic anhydride; and said polybutenyl dicarboxylic compound is reacted with aminoguanidine bicarbonate.

5. The method of claim 4 wherein the polybutenyl substituted dicarboxylic compound is polybutenyl succinic anhydride.

6. The method of claim 5 wherein the polybutenyl substituted succinic anhydride and aminoguanidine bicarbonate are reacted in a mole ratio of about 1.7 to about 2.0 moles of aminoguanidine bicarbonate per equivalent of polybutenyl succinic anhydride.

7. The method of claim 1 wherein the reaction product is treated with a boron-containing compound whereby there is incorporated in the composition about 0.01 to about 5 wt. % boron.

8. The method of claim 7 wherein the dispersant composition incorporates about 0.1 to about 1.0 wt. % boron.

9. The method of claim 8 wherein the dispersant composition incorporates about 0.2 to about 0.7 wt. % boron.

10. The method of claim 1 wherein the triazole is polybutenyl bis-3-amino-1,2,4-triazole.

11. The method of claim 1 wherein the polybutenyl substituent of the succinic anhydride is derived from polybutenyl having $M_n$ of from about 750 to about 1000.

12. The method of claim 1 wherein the polybutenyl substituent of the succinic anhydride is derived from polybutene having $M_n$ of from about 1000 to about 1600.

13. The method of claim 12 wherein the polybutenyl substituent of the succinic anhydride has $M_n$ of about 1150 to about 1350.

14. The method of claim 13 in which the polybutenyl succinic anhydride used to prepare the dispersant is characterized by an SA:PIB ratio of about 1 to about 4:1.

15. The method of claim 14 wherein the SP:PIB ratio is about 1 to about 1.5:1.

16. The method of claim 15 wherein the SA:PIB ratio is about 1.5 to about 2.0:1.

17. The method of claim 14 wherein the SA:PIB ratio is about 1.5 to about 2.0:1.

18. The method of claim 14 wherein the SA:PIB ratio is about 2.5 to about 3.0:1.

19. The method of claim 14 wherein the SA:PIB ratio is about 3.0 to about 4.0:1.

20. The method of claim 1 wherein the polybutenyl substituent of the succinic anhydride is derived from polybutene having $M_n$ of about 1850 to about 2500, and a ratio of $M_w$:$M_n$ of about 1.1 to about 4.

21. The method of claim 20 wherein the polybutenyl succinic anhydride used in preparation of the dispersant is characterized by an SA:PIB ratio of about 1.0 to about 4.0.

22. The method of claim 21 wherein the SA:PIB ratio is about 1 to about 1.5:1.

23. The method of claim 21 wherein the SA:PIB ratio is about 1.5 to about 2:1.

24. The method of claim 21 wherein the SA:PIB ratio is about 2.0 to about 2.5:1.

25. The method of claim 21 wherein the SA:PIB ratio is about 2.5 to about 3.0:1.

26. The method of claim 21 wherein the SA:PIB ratio is about 3.0 to about 4:1.

* * * * *